United States Patent
Soenksen et al.

(10) Patent No.: US 11,315,694 B2
(45) Date of Patent: Apr. 26, 2022

(54) SYSTEM AND METHOD FOR REDUCING ACUTE INCIDENT RISK

(71) Applicant: Ceresti Health, Inc., Carlsbad, CA (US)

(72) Inventors: Dirk Soenksen, Encinitas, CA (US);
Kevin Liang, San Marcos, CA (US);
Mark Wrenn, Oceanside, CA (US);
Tonia Vojtkofsky, Santa Ana, CA (US)

(73) Assignee: Ceresti Health, Inc., Carlsbad, CA (US)

( * ) Notice: Subject to any disclaimer, the term of this patent is extended or adjusted under 35 U.S.C. 154(b) by 1344 days.

(21) Appl. No.: 14/557,918

(22) Filed: Dec. 2, 2014

(65) Prior Publication Data

US 2015/0154372 A1 Jun. 4, 2015

Related U.S. Application Data

(60) Provisional application No. 61/910,803, filed on Dec. 2, 2013.

(51) Int. Cl.
*G16Z 99/00* (2019.01)
*G16H 50/30* (2018.01)
*G16H 50/20* (2018.01)

(52) U.S. Cl.
CPC .............. *G16Z 99/00* (2019.02); *G16H 50/20* (2018.01); *G16H 50/30* (2018.01)

(58) Field of Classification Search
CPC . G06F 19/3437; G06F 19/3431; G10L 15/22; G06Q 10/063112; G06Q 50/22–24; G16H 10/20

See application file for complete search history.

(56) References Cited

U.S. PATENT DOCUMENTS 7,860,725 B2 * 12/2010 Gopinathan ........... A61B 5/411
705/2
7,930,190 B1 * 4/2011 Milanovich ............ G16H 40/20
705/2

(Continued)

FOREIGN PATENT DOCUMENTS

KR 20050054379 A * 6/2005

OTHER PUBLICATIONS

Alzheimer's Association, "2012 Alzheimer's Disease Facts and Figures", Alzheimer's & Dementia (2012) 8(2):1-67, in 72 pages.

(Continued)

*Primary Examiner* — Robert W Morgan
*Assistant Examiner* — Edward B Winston, III
(74) *Attorney, Agent, or Firm* — Procopio, Cory, Hargreaves & Savitch LLP

(57) ABSTRACT

Systems and methods for reducing acute incident risks for dementia patients are provided. Benefits of the systems and methods include reducing healthcare costs, improving patient and caregiver outcomes and reducing caregiver burden. A server system analyzes data related to a dementia patient and the corresponding caregivers (e.g., family member, paid caregiver, physician) and calculates an acute incident risk. Based on the acute incident risk, the server system determines patient therapies to reduce the acute incident risk and also identifies caregiver education to improve the caregiver belief state, which reduces the acute incident risk. The system periodically re-calculates the acute incident risk and identifies patient therapies and caregiver education and motivation to further reduce or maintain the acute incident risk.

24 Claims, 4 Drawing Sheets

(56) References Cited

U.S. PATENT DOCUMENTS

| | | | | |
|---|---|---|---|---|
| 9,560,967 | B2* | 2/2017 | Hyde | A61B 5/0537 |
| 9,649,469 | B2* | 5/2017 | Hyde | A61M 21/02 |
| 2003/0130973 | A1* | 7/2003 | Sumner, II | G06F 19/3437 |
| | | | | 706/45 |
| 2008/0146277 | A1* | 6/2008 | Anglin | G16H 10/60 |
| | | | | 455/556.1 |
| 2011/0077973 | A1* | 3/2011 | Breitenstein | G06Q 10/10 |
| | | | | 705/3 |
| 2011/0131120 | A1* | 6/2011 | Sciuk | G06Q 10/063112 |
| | | | | 705/34 |
| 2012/0053945 | A1* | 3/2012 | Gupta | G10L 15/22 |
| | | | | 704/256 |
| 2013/0059283 | A1* | 3/2013 | Nagaoka | G16H 10/20 |
| | | | | 434/362 |
| 2013/0127620 | A1* | 5/2013 | Siebers | G06K 9/00302 |
| | | | | 340/573.1 |
| 2014/0052475 | A1* | 2/2014 | Madan | G16Z 99/00 |
| | | | | 705/3 |
| 2014/0058755 | A1* | 2/2014 | Macoviak | G16H 10/60 |
| | | | | 705/3 |
| 2014/0113263 | A1* | 4/2014 | Jarrell | G09B 23/28 |
| | | | | 434/262 |
| 2014/0172442 | A1* | 6/2014 | Broderick | G16H 20/30 |
| | | | | 705/2 |
| 2015/0095046 | A1* | 4/2015 | Pironti | G06Q 40/08 |
| | | | | 705/2 |

OTHER PUBLICATIONS

Belluck, "Giving Alzheimer's Patients Their Way, Even Chocolate", The New York Times (2010), in 7 pages.

Center for Medicare Advocacy, "The Changing Demographics of Nursing Home Care: Greater Minority Access . . . Good News, Bad News", (2012), in 3 pages.

Cohen-Mansfield et al., "Engaging nursing home residents with dementia in activities: The effects of modeling presentation order, time of day, and setting characteristics," Aging Ment Health (2010) 14(4):471-480, in 17 pages.

Cohen-Mansfield et al., "The impact of past and present preferences on stimulus engagement in nursing home residents with dementia," Aging Ment Health (2010) 14(1):67-73, in 11 pages.

Cohen-Mansfield et al., "The Comprehensive Process Model of Engagement", Am J Geriatr Psychiatry (2011) 19(10):859-870, in 20 pages.

The Economist, "The reason loneliness could be bad for our health", Healthy living: Mind and body (2011) in 2 pages.

Fleck, "Delay Retirement, Delay Onset of Dementia", AARP Blog Archive, http://blog.aarp.org/2013/07/15/delay-retirement-delay-onset-of-dementia/print/, (Jul. 15, 2013), in 2 pages.

Gerlin, "Vitamins That Cost Pennies a Day Seen Delaying Dementia", Bloomberg Business (2013), in 4 pages.

Gupta, "Can we predict Alzheimer's a decade before symptoms?", CNN.com, http://www.cnn.com/2013/08/17/health/alzheimers-test-eye/, (Aug. 18, 2013) in 4 pages.

Kolanowski et al., "A Randomized Clinical Trial of Theory-Based Activities fore the Behavior Symptoms of Dementia in Nursing Home Residents", J Am Geriatr Soc. (2011) 59(6):1032-1041, in 17 pages.

Owen et al., "Putting brain training to the test", Nature (2010) 465(7299):775-778, in 13 pages.

Reinberg, "Alzheimer's Patients May Mimic Emotions of Those Around them: Study, Findings may have implications for caregivers", HealthDay News for Healthier Living (2013), in 3 pages.

Rockoff, "Lilly Takes Alzheimer's Research Down New Path", The Wall Street Journal (2013), in 3 pages.

Tinker, "'Dementia village' inspires new care", CNN (2013) in 5 pages.

Wang, "Dementia's Cost to Nation Piles Up", U.S. News (2013) in 3 pages.

* cited by examiner

Alzheimer's Disease
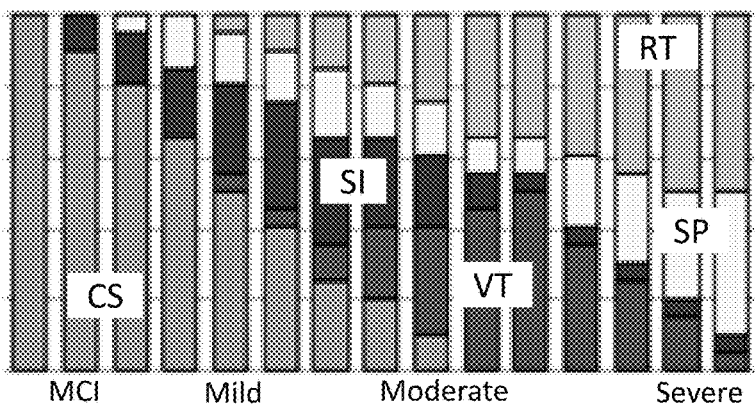
FIG. 7A
Fronto-temporal Dementia
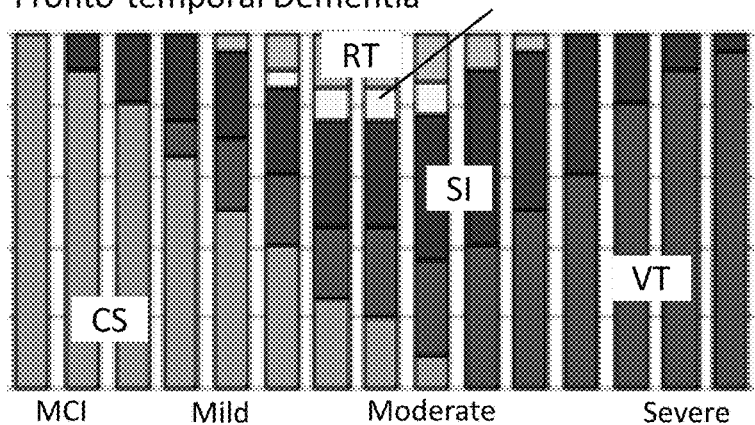
FIG. 7B
Vascular Dementia
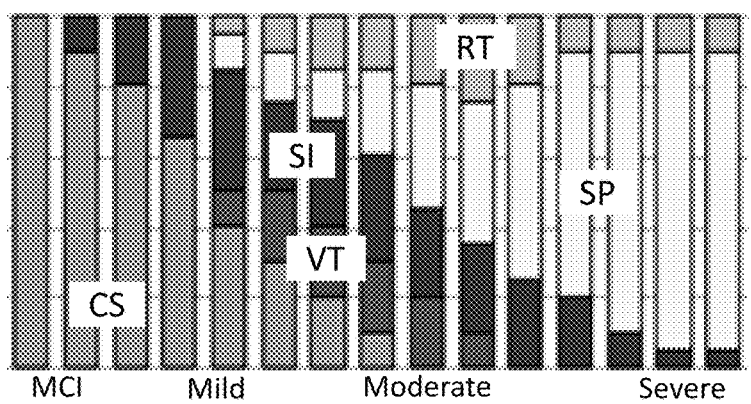
FIG. 7C
Psychosocial Therapies
CS = Cognitive Stimulation
VT = Validation Therapy
SI = Sensory Integration
SP = Simulated Presence
RT = Reminiscence Therapy
FIG. 7D

SYSTEM AND METHOD FOR REDUCING ACUTE INCIDENT RISK

RELATED APPLICATION

The present application claims priority to U.S. provisional patent application No. 61/910,803 filed 2 Dec. 2013 and claims priority to U.S. provisional patent application No. 61/989,264 filed 6 May 2014 and claims priority to U.S. provisional patent application No. 62/047,557 filed 8 Sep. 2014, each of which is incorporated herein by reference in its entirety.

BACKGROUND

Dementia and Alzheimer's Disease (AD), a prevalent type of dementia, are among the most devastating and expensive medical conditions facing mankind, with an estimated annual cost of care that exceeds $200 billion in the U.S., projected to increase six-fold to $1.2 trillion by 2050.

After years of research, remarkably little is known about the causes of dementia and how to detect, prevent or delay it. A systematic review of the scientific literature suggests that best practices for minimizing the likelihood of getting dementia, or slowing the progression of dementia are (i) good nutrition, (ii) physical exercise, (iii) feeling socially connected to family and friends, (iv) minimizing stress and avoiding depression, and (v) cognitive stimulation. The primary focus of the dementia establishment, including the Alzheimer's Association and the White House's National Plan to Address Alzheimer's Disease has been a focus on early detection and a cure.

The focus on early detection and a cure (something experts now believe may still be decades away) has created enormous and immediate financial, emotional and physical challenges for those who already have dementia and those caring for them. The extensive 60+ pages long 2012 Alzheimer's Disease Facts and Figures publication by the Alzheimer's Association provides only two short paragraphs to detail best practices for actively managing dementia. Recommendations are to (i) use available treatment options, (ii) manage coexisting conditions effectively, (iii) coordinate care, (iv) participate in activities, including adult day health care, and (v) participate in support groups and seek counseling. The lack of specificity of these "best practices" highlights the inadequacies of today's best thinking, which is the reason why millions of families taking care of a dementia patients struggle with the devastating impacts of dementia for an average of eight years after initial diagnosis.

Dementia patients are hospitalized three times more frequently than those without dementia and incur Medicare costs that are three times higher and Medicaid costs that are nineteen times higher than patients without dementia. The burden on caregivers is devastating, with 61% reporting high to very high emotional stress and more than half of caregivers dying before the dementia patient, due to the stresses of caregiving.

Medical costs are higher for dementia patients because dementia patients are frequently unable to communicate their needs and symptoms, or have difficulty understanding and following instructions. Many dementia patients also have a higher incidence of comorbidities. Dementia patients are often unnecessarily hospitalized for conditions such as urinary tract infections, constipation/diarrhea, skin issues, delirium, dehydration, malnutrition, and caregiver respite. Once hospitalized, the cognitive impairment of dementia patients results in longer and more expensive hospital stays, which are frequently accompanied by confusion and disorientation and ultimately a rapid decline in patient function.

In general, payers such as health insurance companies do not have much insight into how much money they spend on the care of dementia patients, in part, because many dementia patients suffer from comorbid conditions (e.g., diabetes, chronic obstructive pulmonary disorder (COPD), congestive heart failure (CHF), cancer, etc.) that are more readily identified than dementia, and are thus used by hospitals and physicians for billing purposes. There is also a lack of effective drugs to treat dementia. There are five Food and Drug Administration approved drugs for dementia, but these drugs only provide temporary relief of symptoms. Furthermore, a recent Cleveland Clinic study reported a 99.6 failure rate for AD drugs in the decade from 2002-2012.

SUMMARY

The present disclosure provides systems and methods for reducing the acute incident risk for dementia patients. One embodiment comprises a server device that delivers digital therapies, education, messages and related content to patients and caregivers via patient devices and caregiver devices connected to the server via a network. The systems and methods described herein are effective and scalable, and represent the first holistic solution for reducing acute incident risk for dementia patients. Significant benefits of the systems and methods described herein are to reduce burden and stress for caregivers of dementia patients, increase health-related quality of life (HRQOL) for dementia patients and their caregivers, and reduce costs of healthcare for dementia patients.

Other features and advantages of the present invention will become more readily apparent to those of ordinary skill in the art after reviewing the following detailed description and accompanying drawings.

BRIEF DESCRIPTION OF THE DRAWINGS

The structure and operation of the present invention will be understood from a review of the following detailed description and the accompanying drawings in which like reference numerals refer to like parts and in which:

FIGS. 7A-7D are graph diagrams illustrating example digital personalized psychosocial therapy doses for different types and stages of dementia according to an embodiment;

DETAILED DESCRIPTION

Figure 1:
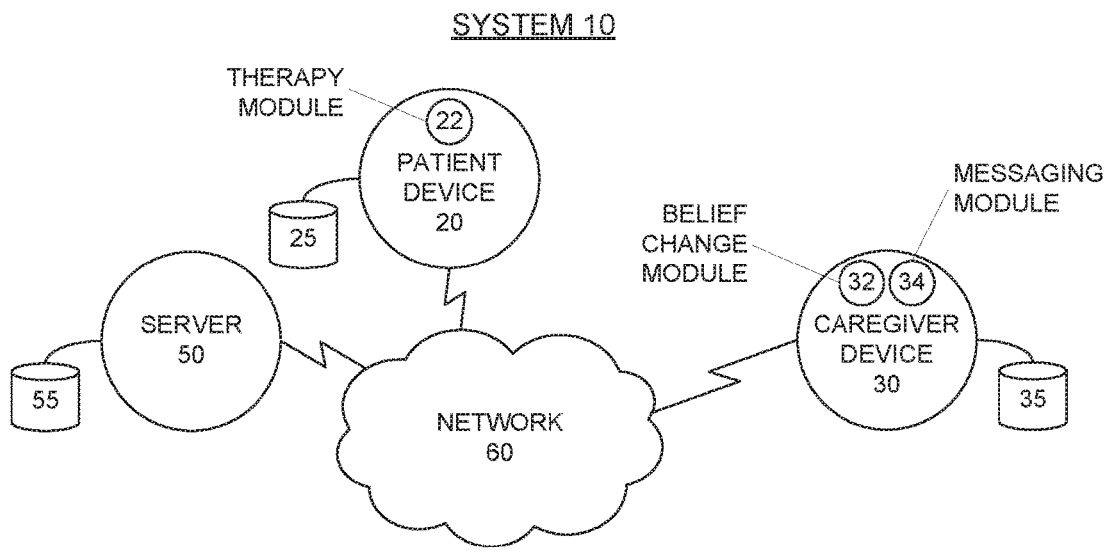
FIG. 1 is a network diagram illustrating an example system for reducing acute incident risk for dementia patients according to an embodiment.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

Certain embodiments disclosed herein provide for systems and methods for reducing the risk of an acute incident for a patient with dementia. For example, a server uses patient profile information stored in memory to determine a personalized digital patient therapy, in accordance with a personalized patient engagement plan, and sends the personalized digital therapy to a patient device via a network. The patient device administers the personalized digital patient therapy to the patient via one or more user interfaces (e.g., audio, visual, and tactile). The personalized digital patient therapy may include psychosocial therapies and cognitive enrichment, which are intended to improve the mood of the patient while reducing negative behaviors. The server also uses caregiver profile information stored in memory to determine a personalized caregiver engagement plan and sends the personalized caregiver engagement plan to a caregiver device via the network. The caregiver device provides the personalized caregiver engagement plan to the caregiver via one or more user interfaces (e.g., audio, visual, and tactile). The personalized caregiver engagement plan may include education or motivational materials to improve the caregiver's engagement and improve the caregiver's belief state.

INTRODUCTION

Dementia is a highly complex disease and has health, behavioral, social and environmental aspects that are extremely challenging, particularly when combined with the additional complexity of managing comorbidities for someone with dementia. The inventors have recognized that dementia is dramatically different than other chronic diseases and major medical conditions (e.g., diabetes, COPD, CHF, cancer), in that dementia affects at least two people: (i) the patient suffering from dementia, and (ii) the caregiver of the dementia patient. In many cases, family, friends and sometimes even physicians become primary and/or secondary caregivers who are also affected by the stress of being involved in the care of a patient with dementia. Dementia is in many ways a family disease.

Dementia is a unique disease because as the patient's cognitive health deteriorates, the patient's ability to participate in conventional patient-centric healthcare similarly deteriorates. Accordingly, as the disease progresses, the primary caregiver increasingly makes healthcare decisions for the dementia patient and other caregivers (e.g., family, physicians) influence those healthcare decisions and also influence the cost, outcomes and quality.

Acute incidents are events that incur healthcare costs. Acute incidents may include hospitalizing a dementia patient, or moving a dementia patient to an assisted living facility or to a nursing home. Avoiding acute incidents, or alternatively, reducing acute incident risk, is particularly important for dementia patients because an acute incident will frequently trigger a "stepwise" decline in the patient's cognitive abilities and/or the patient's ability to perform activities of daily living (ADLs), for example, due to the confusion, disorientation, and stress that the patient experiences as a result of the acute incident.

Health-related quality of life (HRQOL) is a multi-dimensional concept that includes domains related to physical, mental, emotional and social functioning, and focuses on those aspects of overall quality of life that can be clearly shown to affect physical or mental health. HRQOL and well-being are used to measure the effects of chronic illness, treatments, and short- and long-term disabilities. The system described herein increases HRQOL for the patient and caregivers, making it possible for the patient and caregivers to increase their HRQOL notwithstanding the multitude of challenges associated with dementia.

Dementia places extraordinary and often debilitating stress and burdens on the caregiver. Caregiver burden varies based on the type and stage of the patient's dementia, the specific family situation (e.g., local or remote), and the health, competencies and preferences of the caregiver. For example, a patient suffering from mild-stage fronto-temporal dementia may more frequently exhibit new behaviors that will challenge a caregiver more than a mild-stage patient suffering from AD. The system described here in reduces caregiver stress and burden, in part, by increasing caregiver HRQOL and thereby also reduces acute incident risk.

The systems and methods for reducing acute incident risk in dementia patients described herein were recognized by the inventors based on two key insights.

Insight #1. Holistic Solution

Improving healthcare outcomes and reducing costs for dementia requires a holistic solution. A holistic solution is a complete solution that engages the patient and caregivers and encompasses the dementia patient's specific comorbidities such as diabetes, COPD, CHF or cancer. As used herein, caregivers include primary and secondary caregivers (e.g., paid caregivers and family members) as well as any physicians or other medical staff assisting with the dementia patient. The primary caregiver (in some cases a paid caregiver) typically makes most care (and cost) decisions for the dementia patient. Family members influence decisions that are made regarding the dementia patient's care and cost. Physicians and other medical staff treat the dementia patient's comorbidities and thereby impact acute incident risk with appropriate or inappropriate treatment of such comorbidities. Including the dementia patient's comorbidities is an important part of the holistic solution because such inclusion helps to identify and mitigate health risks that can result in costly acute incidents.

Insight #2. Change in Beliefs

Reducing acute incident risk benefits from an improved belief state for all caregivers, with the belief state of the primary caregiver having the most impact on acute incident risk. The inventors recognized that a change in the belief state of caregivers reduces the dementia patient's acute incident risk. In the case of a family disease like dementia, inappropriate caregiver beliefs and concomitant behaviors of caregivers increase acute incident risk, which increases costs, increases caregiver burden and reduces HRQOL.

Conversely, caregivers with appropriate beliefs and concomitant behaviors minimize acute incident risk, which reduces costs, decreases caregiver burden and increases HRQOL.

The inventors also recognized that because people's actions are driven by their beliefs, an important factor in reducing the acute incident risk for dementia patients is for caregivers to have beliefs that promote actions that will reduce the patient's acute incident risk. Additionally, the inventors recognized that because beliefs are formed as a direct result of experiences and because storytelling can be a powerful surrogate for experiences, storytelling is used in caregiver's personalized educational plans to provide caregivers with meaningful experiences that will improve their belief states. Advantageously, positive results—e.g., reducing acute incident risk—also serve as experiences that reinforce the beliefs that led the caregiver to take the actions that led to the positive result in the first instance. This creates a positive feedback loop that promotes continuous improvement.

The inventors have also recognized that a caregiver's belief state can be improved. Advantageously, an improved belief state for a caregiver results in the caregiver taking actions that reduce acute incident risk while also reducing caregiver burden and increasing HRQOL. Accordingly, the caregiver belief state is measured by the system and a personalized caregiver engagement plan is determined that is designed to improve the caregiver belief state. The personalized caregiver engagement plan is determined based on the caregiver's current belief state and willingness to adopt new beliefs or change current beliefs. After delivery of the personalized caregiver engagement plan, the resulting shift of a caregiver's belief state advantageously enables stakeholders to reduce the patient's acute incident risk.

The inventors also recognized that sustained and continuous engagement by caregivers reduces acute incident risk. The guiding principles of the acute incident risk-reducing system are that (i) personalization maximizes engagement and that (ii) engagement drives a change in belief state and the patient's acute incident risk is reduced when engaged caregivers have belief states that cause them to take beneficial actions. The caregiver engagement plan is personalized to the specific needs of each caregiver, and implementation of the system advantageously ensures the ability to cost-effectively deliver acute incident risk reduction to large numbers of dementia patients.

One example of personalization uses personal profile assessment tools to determine caregiver competencies. The system assesses a caregiver's competencies in specific areas required for successful caregiving (e.g., compassion, resilience, responsibility), identifying areas of strength and weakness, and determines a personalized engagement plan for the caregiver that leverages her strengths and minimizes her weaknesses. Personal profile assessments also identify the need for coping strategies for caregivers when operating outside the bounds of their inherent competencies.

FIG. 1 is a network diagram illustrating an example system 10 for reducing acute incident risk according to an embodiment. In the illustrated embodiment, the system 10 comprises a patient device 20 and a caregiver device 30, each of which is communicatively coupled with a server 50 and each other via a network 60. Each of the devices, namely patient device 20, caregiver device 30 and server 50 have associated data storage areas 25, 35 and 55, respectively. The data storage areas may be internal or external and may also be locally or remotely accessed directly or indirectly (e.g., through network 60). In one embodiment, a data storage area is a form of computer memory. In one embodiment, the caregiver device 30 and the patient device 20 are the same device.

Additionally, each of the patient device 20, caregiver device 30 and server 50 can be implemented on a processor enabled device such as later described with respect to FIG. 9. For example, the patient device 20 and caregiver device 30 can be a desktop computer, a laptop computer, a tablet device, a personal communication device (e.g., a smartphone) or the like. In one embodiment, the patient device 20 is an iPad® configured to be "always on" and which provides simple and reliable operation for the dementia patient. An "always on" configuration may also be beneficial for the caregiver device 30, in the case where the caregiver is not technology-savvy. In one embodiment, the patient device 20 and the caregiver device 30 are the same physical device with different operating modes for the patient and the caregiver. In one embodiment, Network 60 can be wired or wireless, public or private and may also include a combination of any of these types of networks. In one embodiment, network 60 includes the Internet.

In one embodiment, patient device 20 includes a therapy module 22 that is configured to operate on the patient device 20 to deliver certain digital therapies to a patient. Such digital therapies can be received via network 60 from the server 50 and administered in real time or stored in memory for later delivery to the patient. For example, therapy module 22 may deliver digital personalized psychosocial therapies (PPT) to the patient via the visual, audio, and tactile user interfaces of patient device 20. In one embodiment, therapy module 22 may deliver digital cognitive enrichment therapies (PCE) to the patient via one or more input and output user interfaces of the patient device 20. For example, a digital cognitive enrichment therapy, which may require more interaction by the patient, may include visual, audio, and tactile output as well as visual, audio, and tactile input.

In one embodiment, caregiver device 30 includes a belief change module 32 that is configured to provide content (e.g., audio, visual, tactile) designed to modify the beliefs of the caregiver in order to improve the belief state of the caregiver. For example, the belief change module 32 may present storytelling videos to the caregiver to enhance the caregiver's experiences and consequently improve the caregiver's belief state.

In one embodiment, the caregiver device 30 also includes a messaging module 34 that is configured to allow a caregiver to send messages to the dementia patient. For example, the caregiver may send words of encouragement to the patient or the caregiver may take a picture and send the picture to the patient. The messaging module 34 also allows a first caregiver to communicate with a second caregiver such as family members or physicians. In one embodiment, the server 50 receives and routes all messages to and from the patient. The server 50 may also review messages prior to delivery to the patient and filter such messages based on patient demographics such as likes and dislikes or current state of awareness/agitation.

Server 50 is configured to implement the system for reducing acute incident risk. In one embodiment, the server 50 is configured to communicate with dementia patients and corresponding caregivers and create and store profiles for each. The server 50 uses the profile information to identify, develop and deliver personalized digital therapies for the dementia patient and to identify, develop and deliver personalized engagement plans for the patient and the caregivers. The personalized engagement plans for the patient are designed to improve the mood of the patient while reducing negative behaviors. The personalized engagement plans for the caregivers are designed to improve the belief state of the caregivers, which in turn results in reduced risk of an acute incident for the patient. Advantageously, the system implements a holistic solution that (a) improves the mood of the patient while reducing negative behaviors, and (b) improves the belief state of caregivers, who in turn make improved healthcare decisions for the patient, which in turn decreases caregiver burden and increases HRQOL for the patient and the caregiver, and also reduces overall healthcare cost.

In one embodiment, system 10 is configured to provide a controlled and stable environment for clinical trials. One of the challenges that pharmaceutical companies have when evaluating the utility of pharmacological interventions for dementia or other neurological disorders is having enough validated information ("signal") to determine beneficial improvements in cognition among the non-validated information ("noise") created by all of the uncontrolled factors that affect a patient's cognitive abilities. A cognitively impaired patient that is under stress, not sleeping, suffering from pain, dehydrated, etc. will score lower on a cognitive assessment than a patient who does not suffer from these symptoms. Similarly, a caregiver who is highly stressed, and whose belief state is low will be more likely to make care decisions (e.g., hospitalization for a cause that is preventable in the home) that will negatively affect the patient's cognition; and may result in a reportable adverse event that will exclude the patient from the study. System 10 is configured to provide a more controlled and stable environment for both the caregiver and the patient, which is desirable for a pharmaceutical company interested in assessing the utility of pharmacological interventions for dementia or other neurological disorders. For example, the system 10 provides the capability to screen caregivers based on belief state and willingness to change beliefs, which allows a pharmaceutical company conducting a clinical study to provide a more controlled and stable environment for the patient within desired tolerances.

Figure 2:
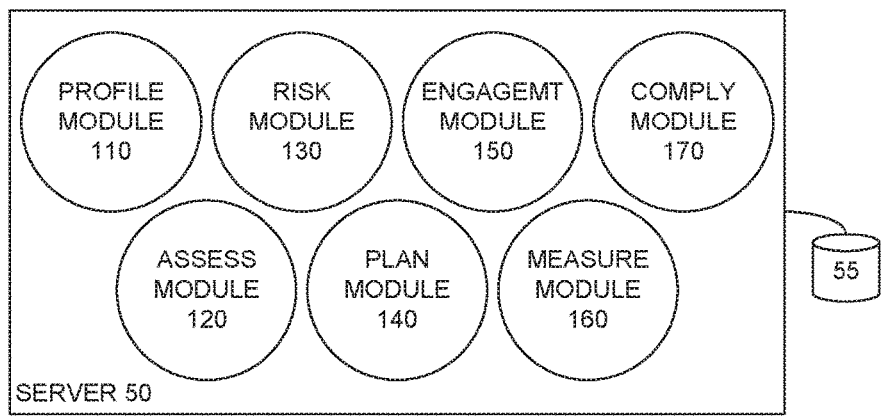
FIG. 2 is a block diagram illustrating an example server in a system for reducing acute incident risk for dementia patients according to an embodiment.

FIG. 2 is a block diagram illustrating an example server 50 according to an embodiment. In the illustrated embodiment, the server 50 comprises a profile module 110, an assessment module 120, a risk module 130, a plan module 140, an engagement module 150, a measure module 160, and a comply module 170. In one embodiment, the server 50 operates on one or more processor enabled devices such as later described with respect to FIG. 9 and resides in a wired or wireless (or some combination of wired and wireless) network system such as previously described with respect to FIG. 1. In one embodiment, the various modules communicate and coordinate with each other both directly (e.g., inter-process communication) and indirectly (e.g., data stored in memory 55).

Profile module 110 is configured to receive detailed information about the patient and caregivers. The profile module 110 receives the information and stores the information in association with a patient or caregiver profile in memory 55. Accordingly, the profile module 110 is configured to create and update patient profiles and caregiver profiles that are stored in memory 55. The patient's profile includes information about the patient's history, personal preferences and specific situation, including the patient's health history (e.g., behaviors, medications), physical and social environments as well as comorbid diseases and conditions. Caregiver profiles are maintained for all caregivers. Caregiver profiles may include information about the caregiver's history, personal preferences and specific situation.

Information about a caregiver's desired benefits resulting from use of the system is also received and stored in the profile. For example, reducing caregiver burden or increasing family connectedness may be a desired benefit for a particular caregiver in one embodiment.

Profile module 110 is also configured to streamline patient and caregiver information into a coherent format to facilitate meaningful retrieval from storage in memory 55, and to support other functions of server 50. Profile module 110 is also configured to cooperate with the other modules of server 50 and provide information to or receive information from such modules as necessary to carry out the various functions of the server 50.

Assessment module 120 is configured to receive patient or caregiver information in addition to the information stored in a corresponding patient or caregiver profile. The assessment module 120 is also configured to analyze the profile and additional information to assess the patient or caregiver. Assessment module 120 is configured to cognitively and functionally assess the patient, for example, using an assessment test such as a computer implemented question and answer session that generates digitally stored results, or a written test that is subsequently scanned into a computer system to similarly generate digitally stored results. In one embodiment, an example of such an assessment test is a Mini-Mental State Examination (MMSE). The MMSE assessment test is designed to determine a patient's current cognitive state. In one embodiment, an example of such a functional assessment test is the Functional Assessment Staging of Alzheimer's Disease (FAST).

Assessment module 120 is configured to communicate with profile module 110 and server 50 to create an electronic cognitive health record for the patient. In one embodiment, the patient's cognitive health record includes cognitive state, medications taken, and responses to digital therapy sessions received by the dementia patient. In one embodiment, the patient's cognitive health record is formatted to enable incorporation into a patient's existing (non-cognitive) medical record. A comprehensive electronic medical record that includes cognitive information facilitates a patient's transition from living at home to living at a care-giving institution (e.g., assisted living facility, continuing care retirement community, skilled nursing facility) by immediately providing paid caregivers and other professionals with access to relevant cognitive information, including preferences. Physician caregivers also benefit by having access to a cognitive health record. Another benefit is that the delivery of the same familiar digital therapies in the home and in the institution eases the transition experienced by a patient moving from the home to an institution.

Assessment module 120 is also configured to determine the current belief state of a caregiver, as well as the caregiver's stress-level and competencies. The activation of physician caregivers is also assessed. Physician activation is an assessment that determines how open a physician is to a patient's involvement in her care. As will be understood by those skilled in the art, patients receive better care from activated physicians. In one embodiment, patient and caregiver assessments are made periodically and the results are stored in memory 55, for example as part of the patient or caregiver profile. The assessment module 120 is also configured to work cooperatively with the other modules in the server 50 to reduce the risk of acute incidents by identifying patient or caregiver needs and initiating corresponding digital therapies or education to address those needs.

Determining the belief state of a caregiver is an important function of assessment module 120 because it establishes a current belief state baseline for which a personalized engagement plan can be developed for the caregiver. An example of Dementia Belief Statements is provided in Table 1. Advantageously, the assessment module 120 is configured to operate in cooperation with other modules of the system 10 to advance a caregiver's belief state to a point where the caregiver's beliefs and corresponding behaviors are aligned with best practices for a dementia caregiver. Such alignment advantageously reduces the risk of an acute patient incident.

TABLE 1

Dementia Belief Statements

| Belief Statement | Detailed Description |
| --- | --- |
| Be Engaged | I engage in the program to improve my quality of life and that of others |
| Plan Ahead | I reduce cognitive health risks by being proactive and well-informed |
| Shift Roles | I have a new role |
| Adjust Expectations | I adjust my expectations to meet my loved ones needs |
| Identify Cause | I investigate the cause of my loved one's symptoms and behaviors |
| Get Involved | I am a valuable and essential member of the care-team |
| Stay Healthy | I take care of myself |
| Seek Help | I have access to support |

Risk module 130 is configured to receive information from profile module 110 and assessment module 120 and determine the dementia patient's acute incident risk. Acute incident risk quantifies the risk of an acute incident such as hospitalization or admission to an assisted living facility or a nursing home.

In one embodiment, the risk module 130 is configured to determine the patient's acute incident risk by assessing the patient. For example, risk module 130 may analyze one or more of: (a) health risks (e.g., dehydration, undiagnosed infection, stress, depression, inadequate pain control); (b) behavioral risks (e.g., physical/verbal aggression, agitation, apathy, lethargy, paranoia); (c) physical environment risk (e.g., unsafe home, inappropriate travel) and (d) social environment risk (e.g., boredom, isolation, family conflict) in the process of determining the patient's acute incident risk.

In one embodiment, the risk module 130 is configured to determine the patient's acute incident risk by assessing both the patient and the caregiver. For example the risk module 130 may analyze the caregiver's decision-making ability, which is determined at least in part by newly received information or stored profile information obtained from memory 55, for example information regarding the caregiver's belief state, competencies, and personal preferences. The caregiver's willingness to change her belief state is also determined by the risk module 130 based on an analysis of stored information from memory 55 or information received from one or more modules such as the assessment module 120. The risk module 130 incorporates the determined willingness of the caregiver to change her belief state into the determination of the patient's acute incident risk. The assessment of the caregiver's decision-making ability quantifies the quality of decisions a specific caregiver will make. A highly stressed caregiver will make decisions that will likely increase acute incident risk. A caregiver with a low belief state and unwillingness to change her beliefs will also make decisions that are likely to increase acute incident risk. On the other hand, a caregiver with a low belief state and a willingness to change her beliefs can improve the quality of decisions over time as her belief state is changed through belief-based educational experiences, and ultimately the caregiver can reduce acute incident risk. It is noteworthy that caregivers of dementia patients have higher stress levels than caregivers of patients with other comorbidities. Dementia caregivers typically give care for an average of eight to ten years at an intensity that is much higher than that of other chronic conditions.

Acute incident risk is a value that is determined by the risk module 130 and comprises and incorporates risk elements for both the dementia patient and the caregiver. Risk factors for the patient include health, behaviors, physical environment and social environment, while risk factors for the caregiver include the caregiver's decision-making ability, which incorporates the caregiver's willingness to change her belief state.

In one embodiment, risk module 130 is also configured to combine the patient and caregiver risk factors into a single value that represents the acute incident risk for the patient and more specifically, for the specific combination of patient and caregiver at a given moment. There are many other risk factors recognized by the inventors that can also be included in the determination of acute incident risk, including for example the activation level of the physician because more activated physicians have patients that are more compliant with treatment protocols. Accordingly, in one embodiment, the risk module 130 is configured to determine the patient's acute incident risk by assessing the patient and a plurality of caregivers (e.g., a primary caregiver and a physician; a primary caregiver and a family member; a primary caregiver and a physician and a family member; or a physician and a family member).

The acute incident risk value determined by the risk module 130 provides significant insight into a complicated patient and caregiver situation at a particular moment in time and allows the system 10 to identify and recommend specific risk-reducing actions, including personalized digital therapies for the dementia patient and personalized engagement plans for the patient and caregivers.

Advantageously, identifying the various risk factors that contribute to the calculation of the acute incident risk value provides immediate and valuable insights into the sources of risk, and where to focus personalized engagement plans. In one embodiment, the system 10 is configured to periodically update risk factors through regular assessments by the assessment module 120 as the patient's dementia progresses, and as the patient develops new comorbidities and symptoms, or as prior comorbidities and symptoms are managed and are hence less impactful on acute incident risk, or as the risk factors that impact a caregiver's decision-making ability change.

Plan module 140 is configured to receive input from at least risk module 130 and is configured to determine a personalized engagement plan for the patient and each caregiver, to amplify the caregiver's competencies and minimize weakness. Personalized engagement plans comprise a prioritized list of engagement activities for the patient and each caregiver. Engagement in the prioritized activities identified in the patient's and each caregiver's personalized engagement plan reduces acute incident risk.

The engagement module 150 is configured to work cooperatively with the other modules of the server 50 to engage the patient and the one or more caregivers. In one embodiment, the engagement module 150 coordinates and cooperates with: (i) education module 210, (ii) activity module 220, (iii) support module 230, (iv) wellness & prevention module 240, and (v) action module 250 in order to develop, optimize and implement personalized engagement plans for a dementia patient and the patient's corresponding caregivers.

Measurement module 160 is configured to coordinate with server 50 to measure and report the activity of the patient on patient device 20 and to measure and report the activity of the caregiver on caregiver device 30. In one embodiment, measurement module 160 is configured to measure and report the total number of minutes of activity in all engagement modes (i.e., education, activity, support, wellness and prevention, action) on the patient device and on the caregiver devices. In one embodiment, measurement module 160 is configured to measure and report the total number of minutes of activity in support mode on the caregiver devices.

In one embodiment, measurement module 160 is configured to coordinate with therapy module 22 on patient device 20 to continuously assess the effectiveness of digital therapies administered to the dementia patient during a digital therapy session. In this case, therapy module 22 is configured to record video imagery of the dementia patient engaging in a digital therapy session and to coordinate with activity module 220 to automatically analyze the facial features and body language of the patient in order to assess the patient's engagement in the digital therapy, as well as the overall effectiveness of the digital therapy. Activity module 220 coordinates with server 50 to update the content of the digital therapy to maximize the effectiveness of the digital therapy session.

Figure 8A:
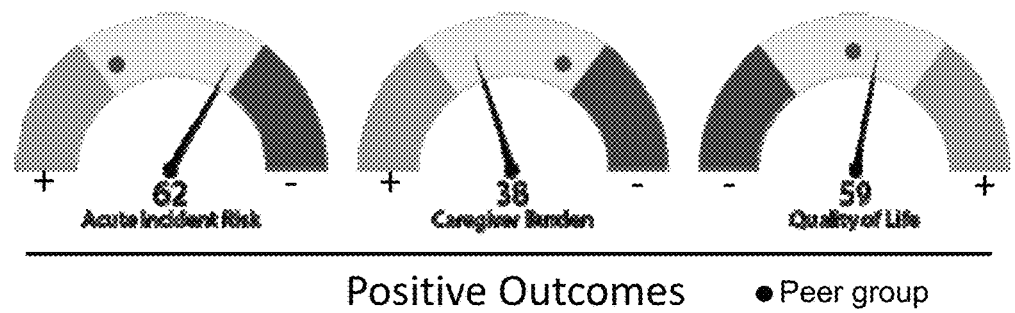
FIGS. 8A-8B are graph diagrams illustrating an example user interface for highlighting positive outcomes and caregiver engagement of the system for reducing acute incident risk for dementia patients according to an embodiment.
Figure 8B:
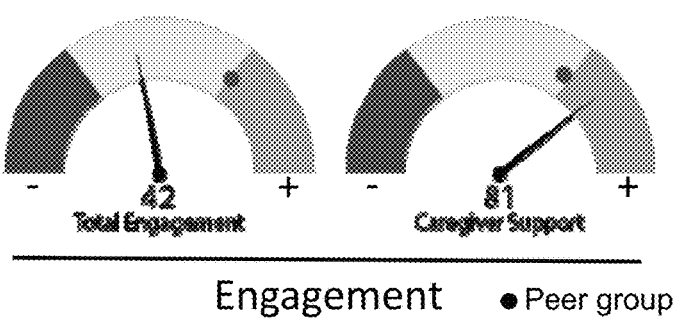

In one embodiment, measurement module 160 is configured to coordinate with server 50 to provide continuous updates about (a) acute incident risk, (b) caregiver burden, (c) quality of life (see FIG. 8A), as well as (d) total engagement, and (e) caregiver support (see FIG. 8B). FIGS. 8A and 8B are an example of an embodiment in which measurement module 160 is configured to present a dashboard on a display of the caregiver device 30 showing a variety of information, for example the above-mentioned measurements. In FIG. 8A, acute incident risk value is 62 and that value is higher than the peer group value (indicated by the dot within the curved bar). However, the caregiver burden value is 38 and that value is lower than the peer group value (indicated by the dot within the curved bar). Similarly, the overall quality of life value is 59 and that value is also higher than the peer group value (indicated by the dot within the curved bar).

In one embodiment, measurement module 160 receives information from one or multiple devices such as pedometers, motion sensors, GPS trackers, calorimeters, blood glucose meters, weight measurement devices, or similar and is configured to integrate such sensory information to increase the utility of the system to reduce acute incident risk for the patient.

In FIG. 8B, the engagement results indicate that the caregiver support value is 81 and that value is higher than the peer group value (indicated by the dot within the curved bar). However, the total engagement value is 42 and that value is lower than the peer group (indicated by the dot within the curved bar). This indicates that the caregivers are not sufficiently engaged to reduce the patient's acute incident risk. For this case, measurement module 160 is configured to coordinate with plan module 130 to update the caregiver engagement plans as needed to reduce acute incident risk for the patient.

Measurement module 160 is also configured to analyze and report data from a large group of patients and caregivers along with related information from the profile module 110 and create peer group metrics corresponding to the measurements reported on the dashboards in FIG. 8A and FIG. 8B. In one embodiment, these peer group metrics are displayed on the dashboards to provide benchmarking information to caregivers and if appropriate, to patients.

Comply module 170 is configured to send reminders about complying with personalized engagement plans to the caregiver device 30 and, if appropriate (e.g., based on the patient's cognitive state), to the patient device 20. In one embodiment, reminders are in the form of audio, visual or text based messages, or auto-generated phone calls. In one embodiment, the form of reminder for any given caregiver or patient is one that is personalized and determined based on information stored in profile module 110.

Advantageously, the collective modules of the server 50 create and manage a database of information in memory 55 related to the patient's disease, including but not limited to physical and cognitive condition, medications taken and digital therapy sessions received. This information is stored in association with the patient assessment and the patient personal profile data. Statistical analysis of the collective database provides insights into the effectiveness of digital therapies across a multitude of dimensions, including combinations with medications taken and other therapeutic regimens being performed. In one embodiment, digital therapy combined with specific medications or therapeutic regimens are analyzed to determine the effectiveness of digital therapies plus medication as compared to the effectiveness of the specific medication alone. Since medications for the brain impact a specific neurotransmitter system, synaptic function or physiological process without having the specificity to target a particular neural region (e.g., the hippocampus), digital therapy can pair regionally specific neural activity (e.g., activation of the pre-frontal cortex with working memory or attention-based digital therapy) with the actions of a particular medication. This combination specifically allows the broad based actions of a particular pharmaceutical compound to be functionally paired and targeted to the appropriate brain region.

Statistical analysis of the collective database also facilitates patient selection for clinical trials. For example, analysis of the database facilitates identification of patients for specific pharmaceutical company-sponsored clinical studies for purposes of evaluating the utility of pharmacological interventions for cognitive decline that occurs prior to MCI, during MCI, during dementia or for other neurological disorders. The ability to identify potential clinical trials subjects based on a variety of factors that can be derived from the database (e.g., cognitive assessment, type of dementia, comorbidity, etc.) provides significant value to pharmaceutical companies who struggle to enroll patients, and provides significant value to patients seeking access to potentially promising treatment regimens.

Figure 3:
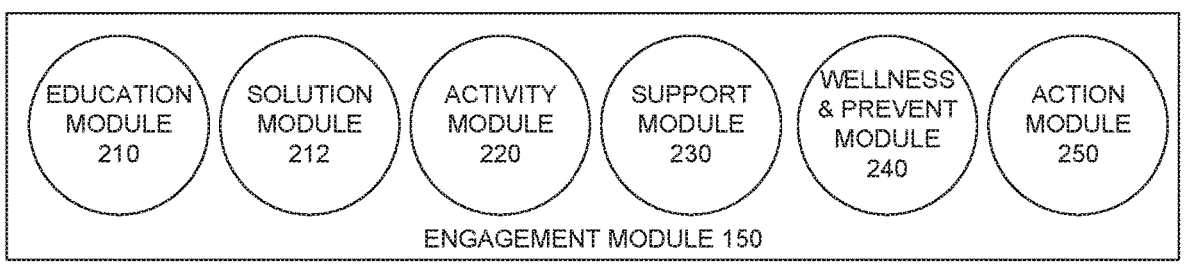
FIG. 3 is a block diagram illustrating an example engagement module according to an embodiment.

FIG. 3 is a block diagram illustrating an example engagement module 150 that is part of the system for reducing acute incident risk according to an embodiment. In the illustrated embodiment, the engagement module 150 comprises an education module 210, a solution module 212, an activity module 220, a support module 230, a wellness and prevention module 240 and an action module 250.

Education module 210 is configured to provide personalized education, referral and training to the caregiver on caregiver device 30. Caregiver education, referral and training is personalized based on the specific challenges associated with providing care to a dementia patient, including the challenges of a specific type of dementia at a specific stage of dementia, and with specific comorbidities. Education module 210 is configured to advance the belief state of the caregiver, which in turn reduces acute incident risk for the patient. While there are many excellent sources of dementia education currently available (e.g., the National Institute of Aging, the Alzheimer's Association), the education module 210 is configured to provide educational content in a personalized manner based on the caregiver's specific current belief state and with the specific aim of improving the caregiver's belief state. Accordingly, unlike general educational content, education module 210 identifies specific educational content for the primary purpose of advancing the belief state of the caregiver and not for the primary purpose of educating the caregiver. The education module 210 is additionally configured to identify education videos that increase the effectiveness of the educational experience for the caregiver, above and beyond the limited benefits of simply reading an article.

Education module 210 is also configured to provide stories that become experiences for the caregiver. These experiences for the caregiver change the caregiver's beliefs and consequently change their belief state. Stories selected by the education module 210 may come from a variety of sources, including other caregivers, families, or dementia experts. Role-playing and acting can also be incorporated into the educational videos to enhance their effectiveness. Education module 210 is configured to deliver educational videos to the caregiver on the caregiver device 30. In the case of a dementia patient who is able to benefit from education, education module 210 can also deliver educational content to the patient via the patient device 20.

Education module 210 is also configured to pace the educational content based on the specific needs of the caregiver or patient, meaning that the content is not delivered all at once, but on an "as needed" basis. In one embodiment, the education module 210 is configured to answer specific caregiver questions (e.g., how to respond to a new patient behavior) by immediately providing the caregiver with the desired information. In one embodiment, a solution module 212 receives requests for information from the education module 210 and is configured to obtain responsive information and send the responsive information directly to the caregiver device 30 or to send the responsive information indirectly to the caregiver device 30 via the education module 210.

Because some caregivers need additional support above and beyond belief-centric educational videos, for example, for caregiver's with a low willingness to change, education module 210 is configured to analyze caregiver information and provide referrals, on caregiver device 30, to local sources of support when warranted. For example, education module 210 may provide referrals, on the caregiver device, to an adult day health care center, or to one or more physicians with a particular specialty, or to one or more support groups, or education module 210 may engage the caregiver in a therapy session with a human therapist using the caregiver device 30 to establish a tele-presence. Education module 210 is also configured to provide the education in the language preference of the caregiver.

In one embodiment, the education module 210 coordinates collaborative communication for multiple caregivers, each through their respective caregiver device 30, to enable the plural caregivers to participate in a virtual caregiver support group. Advantageously, the education module 210 is configured to analyze caregiver profiles to identify and optimize virtual support groups with selected caregivers that are matched along common dimensions such as personality, situation, personal preferences, belief state and willingness to change. Caregivers that are matched appropriately will be more effective, e.g., they will engage with one another to communicate effectively, listen to one another and contribute to reducing their relative stress levels, and assist one another in increasing their respective belief state. Virtual support groups are not limited to primary caregivers, and similar virtual groups could be formed for all types of caregivers, including family members and friends and even patients.

Figure 6:
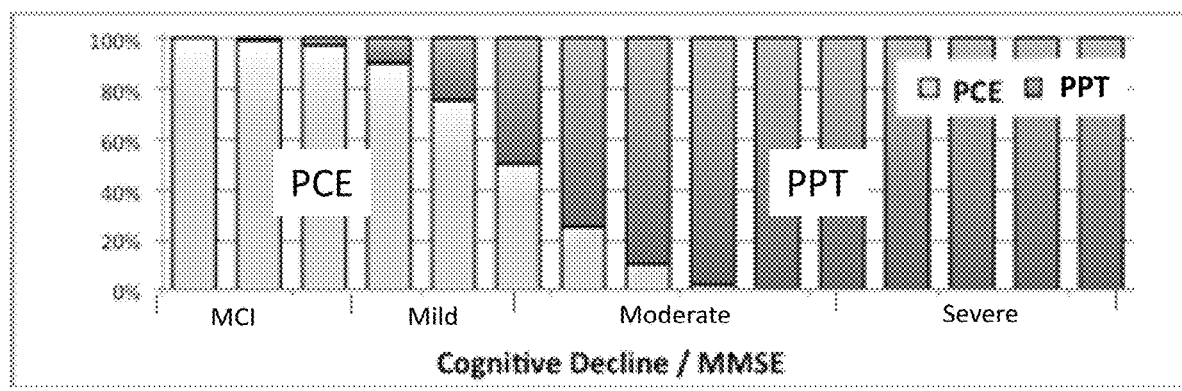
FIG. 6 is a graph diagram illustrating example digital personalized cognitive enrichment and digital personalized psychosocial therapy doses as a function of the cognitive state of a patient's Mini-Mental State Examination assessment according to an embodiment.

Activity module 220 is configured to provide the patient with continuous access to digital therapies via the therapy module 22 on the patient device 20. Digital therapies include digital personalized psychosocial therapies (PPT) for dementia and digital personalized cognitive enrichment (PCE), with digital PCE being more interactive than digital PPT. In one embodiment, digital PPT comprises validation, reminiscence, sensory integration, simulated presence and cognitive stimulation while digital PCE comprises primarily cognitive stimulation and is therefore more suitable for patients at earlier stages of dementia. The graph diagram illustrated in FIG. 6 shows an example dosing of digital PCE and digital PPT for patients at different stages of cognitive decline. As can be seen, digital PCE is not incorporated into the prescribed digital therapies at the more advanced stages of dementia due to the ineffectiveness of cognitive stimulation at the later stages of dementia.

Activity module 220 is also configured to identify non-digital activities to engage the patient (e.g., crafts, puzzles, singing, dancing), including activities that can be conducted jointly between the patient and caregivers. The list of such activities is determined by activities module 220 based on the patient's type and stage of dementia, comorbid conditions and personal preferences, and is updated continuously as the disease progresses to reflect the patient's changing needs and preferences.

Digital therapies are an important aspect of reducing acute incident risk for dementia patients because the digital therapies manage a patient's behavioral symptoms, which are often the direct result of the level of agitation displayed by the patient. In institutional environments such as assisted living facilities, skilled nursing facilities or nursing homes, improving patients' HRQOL while reducing the burden, stress and high cost of behavioral symptoms is a critical unmet need of paid caregivers of patients with dementia. In such environments patient agitation can pose a challenge to nursing staff (sometimes resulting in worker's compensation claims), and can lead to the use of anti-psychotic drugs (chemical restraints) to calm patients, the use of physical restraints or re-hospitalization. All of the consequences of negative patient behaviors increase acute incident risk for dementia patients. A recent mandate by the Centers for Medicare and Medicaid Services (CMS) for skilled nursing facilities is to reduce the use of anti-psychotropic drugs (e.g., Seroquel, Risperdal) and this mandate is also likely to exacerbate the behavior challenges of dementia patients living in nursing homes.

Studies show that effective personalized engagement of dementia patients reduces agitation and the resulting negative behaviors, while increasing patients' HRQOL. Dementia-related behaviors are most likely to occur during periods of unoccupied time or of boredom. Residents in nursing homes are left alone 85% of the time, according to some studies. Under-stimulation of dementia patients magnifies the apathy, boredom, depression and loneliness that is typically associated with dementia. Engagement in activities has been shown to have a positive effect on dementia patients and reduce negative behaviors. Observable benefits of engagement include (a) marked increase in measured happiness, (b) elevated interest and alertness, (c) decrease in boredom, (d) improvement in performance of activities of daily living, (e) improved cognition and attention, and (f) higher quality of life. Advantageously, the activity module 220 is configured to personalize the digital and non-digital activities for the specific dementia patient based on the patient's type and stage of dementia, comorbid conditions and personal preferences to optimize the effectiveness of patient activities.

Activity module 220 is configured to personalize digital therapies and non-digital activities using personalized and personally relevant content, which includes video, images, pictures, music, voice messages that are personal to a specific patient. In one embodiment, such content is stored in memory as part of a patient's profile. In cases when individually relevant content can be obtained, activity module 220 is configured to create an effective personalized digital therapy, but when such content is not available, activity module 220 is configured to utilize content from a personal preference content library to develop the personalized digital therapy. Personal preference content is content that is matched to the patient's personal preferences, but which is not personalized in the sense that it includes content from the patient's life memories (e.g., a picture of the patient's spouse, children or other loved ones). Consequently, an individual's personalized digital therapy may comprise a mix of personal content and personal preference content from a library; and the activity module 220 seamlessly combines personal content and personal preference content into a dynamically created personalized digital therapy, and continuously incorporates new personal content and new personal preference content into the dynamically created personalized digital therapy.

Activity module 220 is configured to maximize the effectiveness of personalized digital therapy. Specifically, activity module 210 is configured to receive (a) a comprehensive patient questionnaire that is completed by family, friends and other caregivers, and (b) the patient's cognitive assessment (e.g., MMSE). In one embodiment, the comprehensive questionnaire includes basic demographic information and also includes life memories (e.g., family, friends, hobbies, music, etc.) and information about family dynamics, interests, cognitive capabilities, physical capabilities, personality, culture, language, known medical conditions/diagnoses/symptoms, as well as information about negative triggers that should be avoided.

In one embodiment, activity module 220 is configured to deliver personalized digital therapy as a sequence of digital media elements, with each digital media element comprising at least one type of psychosocial therapy. Examples of digital media elements include a family element focused on reinforcing the family relationships for an individual with dementia or AD. Other elements include favorite activities and past-times, major life events, job functions, relaxation, smiling, and sleep, just to name a few.

In one embodiment, activity module 220 is configured to determine an appropriate, and ideally an optimal, mix of digital therapies for any given patient based on the information contained in the comprehensive questionnaire, cognitive assessment, patient profile and caregiver profiles. The appropriate mix of digital therapies will differ from patient to patient based on many factors, including cognitive capabilities and physical capabilities. The appropriate mix of digital therapies will also change over time as the cognitive and physical capabilities of the patient change over time. In the case of someone with dementia or AD, their cognitive capabilities will decline over time, and therefore the appropriate mix of digital therapies will also change over time. In one embodiment, the activity module 220 continuously adapts the appropriate mix of elements included in the digital therapies based an individuals' changing cognitive capabilities as well as changes in other neural and physical capabilities.

In one embodiment, activities module 220 is configured to provide the patient with an appropriate mix of digital therapies based on the patient's ability to interact with the patient device 20. In one embodiment, the patient device 20 comprises a touch-screen interface. Some patients may be capable and comfortable interacting with a keyboard/mouse or a touch-screen interface, while others may not be capable and/or comfortable doing so. For some patients, the most beneficial digital therapy may be voice-activated, or based on eye-movements as determined by eye-tracking or even feedback provided from real-time physiological recordings from the brain (e.g., electroencephalography (EEG)) or body (e.g., blood pressure, heart rate) or other biometric information.

For institutional use, it may be more desirable to deliver digital therapies using a patient device 20 that is attached to a cart with wheels, so that the delivery platform can be easily moved from room to room. In one embodiment, digital therapy is integrated into an autonomous robotic platform based on a pre-determined schedule of patients to be visited and their corresponding locations; or based on commands from a mobile device. Similarly, patient device 20 can be used to provide real-time access to remotely located caregiver devices to gain access to friends, family and other caregivers as well as therapists that conduct specific therapies (e.g., speech therapy) in a telemedicine/telepresence environment.

In one embodiment, activity module 220 provides scheduling support for the staff of an institution that is using the digital therapies created by the activity module 220. More specifically, in one embodiment, activity module 220 is configured to determine the order of the patients that are to receive digital therapy and to facilitate the deployment of multiple patient devices 20 attached to multiple mobile carts operating in the same or different facilities. The activity module 220 is also configured to adapt the content included in a digital therapy for the language preference of the patient.

The personalized digital therapy created by the activity module 220 is beneficial to individuals suffering from any type of neural or cognitive impairment, and is not limited to patients suffering from dementia or AD. For example, personalized digital therapy could be useful for patients suffering from stroke, post-traumatic stress disorder (PTSD), attention deficit disorder (ADD), addiction, depression/anxiety disorders or any other brain based conditions, or even healthy individuals who are worried about their cognitive health. The ability to configure activity module 220 to deliver an appropriate "dose" of personalized digital therapies for any type of cognitive disorder, creates a scalable, tunable platform for the delivery of precisely targeted neural stimuli to desired brain regions. This regional targeting of different brain regions using personalized digital therapy based on the patient's specific condition or needs is a unique feature of the system. Combination of regional targeting of different brain regions using personalized digital therapy with pharmaceutical drugs is also a unique feature of the system.

Support module 230 is configured to send audio, image, video or text messages received by the messaging module 34 on the caregiver device 30 to the patient device 20. The ability for each caregiver (e.g., family, friends and physicians) to have an easy and efficient means of communicating with the primary caregiver and/or the patient is critical to reducing acute incident risk because the messages of support for the caregiver are intended to serve as positive, desirable feedback that will motivate and inspire the caregiver to follow the personalized engagement plan provided by plan module 140. Accordingly, the support module 230 reinforces the motivation of the caregiver to reduce acute incident risk for the patient by implementing a social platform for delivering messages of support, reminders, and other encouragement. The support module 230 similarly encourages the patient by delivering messages of support that increase the patient's sense of connectedness to family and friends, which advantageously reduces one of the specific known risk factors for developing dementia or advancing the stages of dementia.

Support module 230 is configured to send periodic updates to and receive information from one or more caregiver devices 30 about specific accomplishments in caregivers' and the patient's personalized engagement plan. Support module 230 is further configured to send reminders to other caregivers requesting the other caregivers (e.g., family and friends) to send audio, image, video or text messages of support to the primary caregiver and/or the patient. In one embodiment, the support module 230 is configured to allow the caregiver to reply to a message of support using emoticons, e.g., caricatures of happy and sad "faces" that can express a plurality of emotions. In one embodiment, support module 230 is configured to allow the patient to reply to a message of support using emoticons. Replies using emoticons are preferred when the caregiver or patient are not technology-savvy enough or physically capable to provide tactile input to the caregiver device 30 or to the patient device 20. In one embodiment, replies using only emoticons are enforced by the support module 230 to reduce the stress and/or burden of responding more fully or to reduce the frustration of not being physically able to respond more fully.

In one embodiment, support module 230 is configured to continuously display audio, image, video or text messages on the caregiver device 30 and/or the patient device 20, for the continuous enjoyment of the caregiver and the patient.

In one embodiment, the caregiver has access to multiple caregiver devices 30 that could be located in different rooms in the caregiver's home. Similarly, in one embodiment the patient has access to multiple patient devices 20 that could be located in different rooms in the patient's home. In one embodiment, the caregiver device 30 and patient device 20 are co-located in the one home.

In one embodiment, support module 230 is configured to send information about the patient's digital therapy sessions to one or more caregiver devices 30. In one embodiment, such information comprises data about the effectiveness of the digital therapy sessions. In one embodiment, support module 230 is configured to store a picture of the patient taken by patient device 20 at the end of a digital therapy session in memory 55 and optionally to send the picture to one or more caregiver devices 30.

In one embodiment, support module 230 is configured to receive additional personalized content, suitable for current or future digital therapy sessions, and store such content in memory 55. In one embodiment, support module 230 is configured to show a "content gauge" on caregiver device 30 to indicate the need to receive additional personalized content from caregivers or the existence of a surplus of personalized content.

Support module 230 is also configured to display an enhanced digital therapy session on a caregiver device 30, which includes simultaneous display of the recorded video of the patient watching their digital therapy, in conjunction with the display of the patient's digital therapy. In this fashion, the caregiver can see the patient's facial expression responses and hear the patient's audible responses to specific elements of the patient's digital therapy session. In one embodiment, support module 230 is configured to color-code the enhanced digital therapy session, by type of psychosocial therapy employed in the patient's digital therapy, and optionally in combination with a measure of the patient's engagement in their digital therapy, for example, as determined by analyzing the patient's eye movements. In one embodiment, support module 230 is configured to display an image of the human brain highlighting regions of the brain that are stimulated by a specific psychosocial therapies of the patient's digital therapy session, in synchrony with the patient's digital therapy session.

Wellness and prevention module 240 is configured to provide education, referral and training about wellness and disease prevention to one or more caregiver devices 30 and if appropriate (e.g., based on the patient's cognitive state), to the patient device 20. In one embodiment, the specific wellness and prevention education is presented to caregivers in accordance with recommendations outlined in the personalized engagement plans created by plan module 140 for each caregiver. In one embodiment, wellness and prevention education is presented using the same types of educational video that are employed by the education module 210. Increasing caregiver wellness, for example, via physical exercise, better nutrition, or increased socialization, and preventing disease, for example, by having regular physicals or conducting a home safety inspection, is beneficial to reduce the patient's acute incident risk. Exercise and good nutrition are known risk factors for dementia, as are being socially connected, minimizing stress and engaging in cognitively stimulating activities. The Wellness & Prevention module 240 is configured to engage all caregivers in activities that will reduce acute incident risk for the patient.

Action module 250 is configured to provide education, referral and training about other actions that can reduce acute incident risk, and specifically actions that do not fall within the scope of the education module 210 or the wellness and prevention module 240. The action module 250 is configured to provide such education, referral and training to one or more caregiver devices 30 and if appropriate (i.e., based on the patient's cognitive state), to the patient device 20. In one embodiment, the specific materials presented to the various caregivers are consistent with recommendations outlined in the personalized engagement plans created by plan module 140 for each caregiver. In one embodiment, action module 250 is configured to provide information and materials related to financial and estate planning, referrals to assisted living, and establishing advanced directives in the event the patient is hospitalized.

Figure 4:
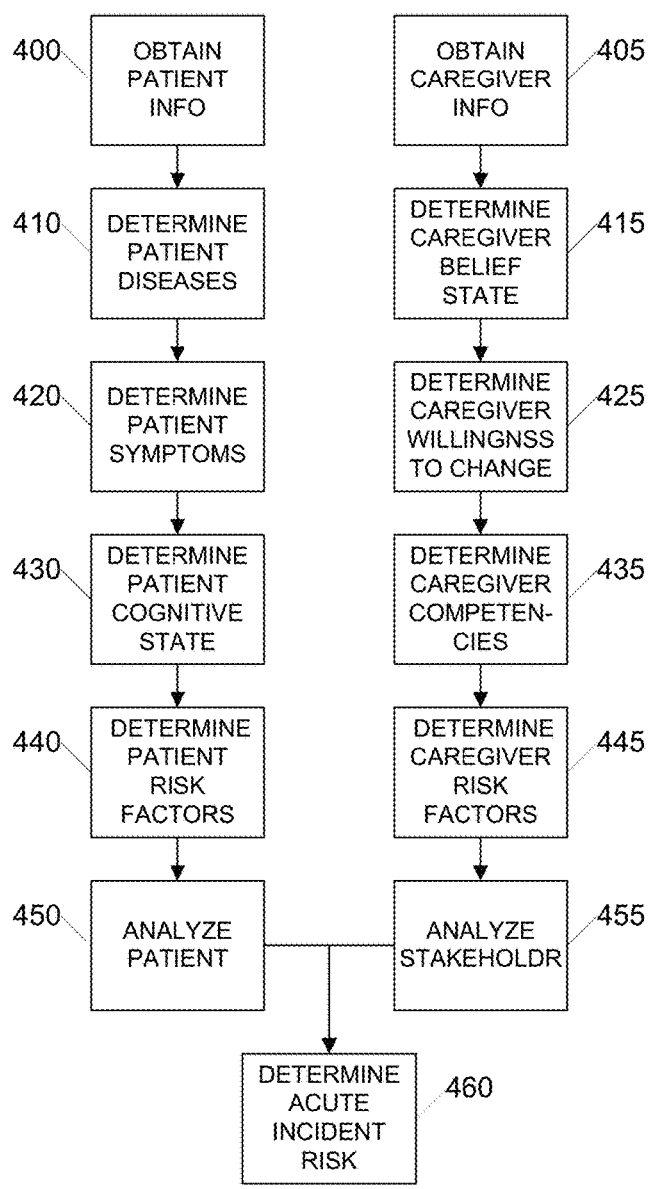
FIG. 4 is a flow diagram illustrating an example process for determining acute incident risk according to an embodiment.

FIG. 4 is a flow diagram illustrating an example process for determining acute incident risk according to an embodiment. In one embodiment, the illustrated process can be carried out by a system such as previously described with respect to FIGS. 1, 2 and 3. The illustrated process shows steps that can take place in parallel with respect to a patient and a caregiver (e.g., paid caregiver, physician, family member). The steps may also take place serially and can be performed in a different order than the order presented in FIG. 4.

On the patient path, initially in step 400 the system obtains information about the patient. Such information may include information about the patient's history, demographic information, personal preferences and specific situation, including the patient's health history (e.g., behaviors, medications, genetics), physical and social environments as well as comorbid diseases, conditions and symptoms, and historical information about prior assessments for the patient and the results of prior digital therapy sessions. Next, in steps 410 and 420 the system determines the current diseases and symptoms of the patient that contribute to the patient's acute incident risk. Examples of symptoms that contribute to acute incident risk include impaired vision, impaired hearing, impaired breathing, pain, dizziness, wandering, loss of balance, dehydration, malnutrition, insomnia, and fainting. In step 430 the system determines the elements of the patient's cognitive state that contribute to acute incident risk. Cognitive state includes the type and stage of the patient's dementia as well as the patient's functional level, for example, as measured using MMSE or FAST assessments and an assessment of ADLs. Next, in step 440, the system identifies one or more patient risk factors based on an analysis of the patient information, patient diseases, patient symptoms and patient cognitive state and determines the degree to which each identified patient risk factor contributes to acute incident risk. Risk factors may include health risks, behavioral risks, physical environment risks, and social environment risks, just to name a few. Once all of the information and other data about the patient has been obtained or determined, the system analyzes the patient information and other data as shown in step 450 to determine the contribution to acute incident risk due to patient risk factors.

Similarly, in step 405 the system obtains information about one or more caregivers. Such information may include one or more caregiver profiles that contain information about the caregiver's history, health history, personal preferences and specific situation, demographic information and historical information about prior assessments for the caregiver. Next, in steps 415 and 425 the system determines the belief state for the one or more caregivers and the caregiver's willingness to change her belief state. In step 435 the system determines the caregiver's competencies. In one embodiment, the system determines which of the approximately seventy-three human competencies that describe the human condition are most relevant to the patient's acute incident risk. Examples of caregiver competencies include compassion, resilience, tolerance, and adaptability, just to name a few. Next, the system identifies one or more caregiver risk factors based on an analysis of the caregiver information, caregiver belief state, caregiver willingness to change and caregiver competencies and determines the degree to which each identified caregiver risk factor contributes to acute incident risk. Caregiver risk factors can include the caregiver's decision-making ability. In the case of a physician, the caregiver risk factors can include the physician activation level. In the case of a family member, the caregiver risk factors can include influence over the primary caregiver. Once all of the information and other data about the caregiver has been obtained or determined, the system analyzes the caregiver information and other data as shown in step 455 to determine the contribution to acute incident risk due to caregiver risk factors. Finally, in step 460 the system determines an acute incident risk for the patient based on the analysis of the patient information and data and the analysis of the caregiver information and data. In one embodiment the acute incident risk is determined as a numerical value.

Figure 5:
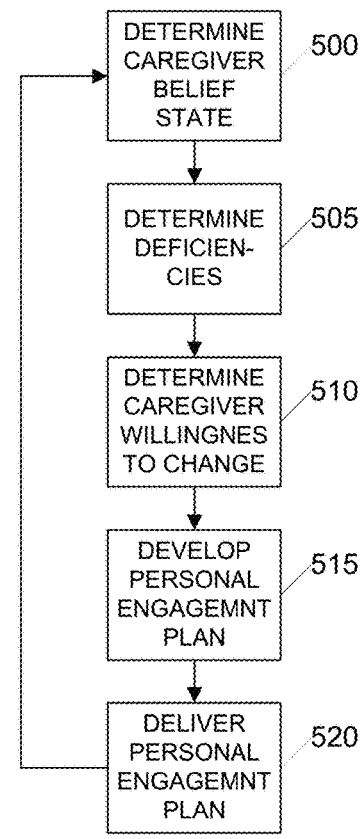
FIG. 5 is a flow diagram illustrating an example process for modifying belief state according to an embodiment.

FIG. 5 is a flow diagram illustrating an example process for modifying belief state according to an embodiment. In one embodiment, the illustrated process can be carried out by a system such as previously described with respect to FIGS. 1, 2, 3 and 4. The illustrated process shows steps that take place with respect to a caregiver (e.g., paid caregiver, physician, family member). The steps may also take place serially and can be performed in a different order than the order presented in FIG. 5.

In step 500 the system determines the caregiver belief state, which is a measure of the extent to which the caregiver embraces the dementia belief statements detailed in Table 1. The deficiencies in caregiver belief state are determined in step 505 and represent a detailed "gap analysis" of the caregiver's agreement with each specific dementia belief statement. The caregiver's willingness to change beliefs is determined in step 510. The caregiver's willingness to change can be determined using a variety of personal profile assessments. In one embodiment the commercially available Rembrandt Advantage on-line personal profile assessment is used to determine the caregiver's willingness to change.

A personal engagement plan for the caregiver is developed in step 515 based on the prior determination of caregiver belief state and caregiver willingness to change. The personal engagement plan is developed to improve the caregiver's belief state by focusing on the specific dementia belief statements in which the caregiver is deficient. The personal engagement plan is delivered to the caregiver, in step 520, on the caregiver device 30.

In one embodiment, the personal engagement plan is delivered in the form of educational videos that are selected to advance the specific belief states in which the caregiver is deficient. The determination of the caregiver's willingness to change influences the personal engagement plan in that a "willing" caregiver's belief state can be moved with a relatively smaller number of educational videos. In contrast, an "unwilling" caregiver will be provided with more educational videos, as well as referrals to "peer" support groups and one-to-one video conferencing with a personal coach or mentor. The dashboard (previously described with respect to FIGS. 8A-8B) summarizing the patient's acute incident risk, the caregiver burden and quality of life also provide positive motivation for the caregiver to continue to follow her personal engagement plan.

Following the delivery of the personal engagement plan or portions thereof, whether in the form of educational videos, referrals to support groups, video conferencing, or updated dashboard, the caregiver's belief state will improve. The process periodically loops back to subsequently assess the caregiver's belief state again in step 500, and the process of determining deficiencies, determining willingness, developing a personalized engagement plan and delivering the various elements of the engagement plan is repeated based on the newly determined belief state for the caregiver.

FIG. 6 is a graph diagram illustrating example digital therapy doses as a function of the cognitive state of a patient's MMSE assessment according to an embodiment. In the illustrated embodiment, the digital therapies include personalized cognitive enrichment (PCE) and personalized psychosocial therapy (PPT). As shown in the graph, as a patient's cognitive state declines, the relative amount of digital PPT is increased in order to engage the patient. Similarly, for a patient at the mild cognitive impairment (MCI) stage, more cognitively challenging digital PCE is required to engage the patient. The FIG. 6 graph illustrates the advantage provided by the adaptive capability of the system that allows the dosing of PPT and PCE digital therapies to be determined and administered based on the specific and current needs of a patient.

FIGS. 7A-7D are graph diagrams illustrating example digital PPT doses for different types and stages of dementia according to an embodiment. FIG. 7A is an example of how digital therapies are dosed in one embodiment for a patient with AD based on the stage and type of dementia and digital PPT defined in FIG. 7D. FIG. 7B is a similar example for fronto-temporal dementia, and FIG. 7C is for a patient with vascular dementia. The five psychosocial therapies described in FIG. 7D are presented by way of example only and are not the only psychosocial therapies that are known to be effective for dementia patients. For example, in one embodiment, activity module 220 can be configured to accommodate other types of psychosocial therapies and other types of digital therapies, for example, habilitation therapy, art therapy or music therapy.

The appropriate mix of digital therapies is designed to change for a specific patient over time. For example, the most appropriate digital therapy delivered in the morning may not be the most appropriate digital therapy provided in the afternoon or evening, particularly if the dementia patient suffers from sundowners or certain sleep conditions. Similarly, the appropriate mix of digital therapies may change over time (e.g., from session to session or day-to-day), or may not change very often, depending on the capabilities and personalized needs of the dementia patient. Advantageously, activity module 220 is configured to be adaptive to the patient's changing needs for digital therapies such as PPT and PCE.

FIGS. 8A-8B are graph diagrams illustrating an example user interface for highlighting positive outcomes and engagement of the system for reducing acute incident risk in dementia patients according to an embodiment. As previously described, FIG. 8A illustrates the (a) acute incident risk value, (b) caregiver burden value, (c) quality of life value, collectively the positive outcomes. The user interface advantageously shows the three positive outcomes values in relation to the peer group value for the same metric. Similarly, FIG. 8B illustrates (a) total engagement and (b) engagement in caregiver support, collectively the engagement. The user interface advantageously shows the two engagement values in relation to the peer group values for these same metrics.

Cost Benefits

An estimated 12.3 million people aged 65+ currently living in the U.S. have some form of cognitive impairment. Of these 12.3 million people, 4.9 million have Mild Cognitive Impairment (MCI), often a precursor to dementia, and 7.4 million have AD or some other type of dementia, growing at 4.5% annually. Of the 7.4 million with AD/dementia, an estimated 3 million have mild dementia, 2.6 million have moderate dementia and 1.8 million have severe dementia. The number of people with dementia that live in an assisted living facility or in a skilled nursing facility increases as the disease progresses. 5.7 million people currently live with cognitive impairment at home, reflecting the desire by the vast majority of seniors to age in place.

Fueled by an aging U.S. population in which the 85-year and older segment is growing most rapidly, the number of people with dementia aged 65+ is expected to triple from 7.4 million people today to more than 20 million by 2050, with an expected cost of care to exceed $1.2 trillion annually.

Patients suffering from dementia are hospitalized three times more frequently than those without dementia and incur Medicare costs ($107 billion) that are three times higher and Medicaid costs ($35 billion) that are nineteen times higher than patients without the disease.

Dementia is a family disease that also takes a devastating toll on family caregivers who provide 80% of the care for a client. An estimated 15 million family caregivers currently provide 17 billion hours of unpaid care, valued at $216 billion. 61% of caregivers report high to very high emotional stress of caregiving and 37% rate stress as their primary challenge. Almost 50% of caregivers suffer from depression and many become secondary patients, incurring $9.1 billion in additional annual healthcare costs.

Table 2 summarizes the average annual per-person payment for health care services provided to Medicare beneficiaries age 65+, according to data from the Alzheimer's Association.

TABLE 2

Average Annual Per-Person Payment for health care services provided to Medicare beneficiaries age 65+

| Expense Type | With Dementia | Without Dementia | Difference |
| --- | --- | --- | --- |
| Inpatient Hospital | $10,293 | $4,138 | $ 6,155 |
| Skilled Nursing | $ 3,995 | $ 460 | $ 3,535 |
| Home Health | $ 1,460 | $ 471 | $ 989 |
| Total | $15,708 | $5,069 | $10,639 |

The presently described systems and methods are advantageously capable of completely eliminating, or partially eliminating, the incremental costs of dementia by reducing acute incident risk for dementia patients. The presently described systems and methods therefore represent a total potential cost savings of $60 billion annually for the 5.7 million seniors currently living at home in the United States with some level of dementia. A more practical and realistic estimate is that the presently described systems and methods can save 50% of the incremental costs of dementia for 50% of the 5.7 million seniors currently living at home. In this more practical and realistic instance, the cost savings would be $12.5 billion every year. As the global population ages and more individuals are diagnosed with dementia, the potential costs savings of the presently described systems and methods will have a significant impact on reducing healthcare costs in the United States and around the world.

Figure 9:
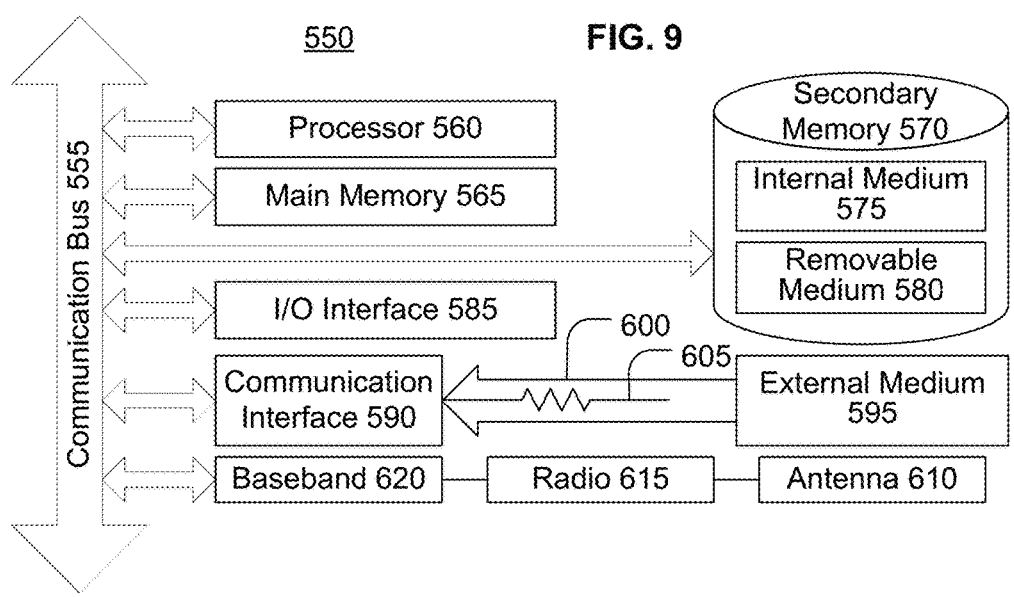
FIG. 9 is a block diagram illustrating an example wired or wireless processor enabled device that may be used in connection with various embodiments described herein.

FIG. 9 is a block diagram illustrating an example wired or wireless system 550 that may be used in connection with various embodiments described herein. For example the system 550 may be used as or in conjunction with processor enabled devices such as the server, patient device, caregiver device and stakeholder device as previously described with respect to FIGS. 1 and 2. The system 550 can be a conventional personal computer, computer server, personal digital assistant, smart phone, tablet computer, or any other processor enabled device that is capable of wired or wireless data communication. Other computer systems and/or architectures may be also used, as will be clear to those skilled in the art.

The system 550 preferably includes one or more processors, such as processor 560. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 560.

The processor 560 is preferably connected to a communication bus 555. The communication bus 555 may include a data channel for facilitating information transfer between storage and other peripheral components of the system 550. The communication bus 555 further may provide a set of signals used for communication with the processor 560, including a data bus, address bus, and control bus (not shown). The communication bus 555 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

System 550 preferably includes a main memory 565 and may also include a secondary memory 570. The main memory 565 provides storage of instructions and data for programs executing on the processor 560. The main memory 565 is typically semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The secondary memory 570 may optionally include a internal memory 575 and/or a removable medium 580, for example a floppy disk drive, a magnetic tape drive, a compact disc ("CD") drive, a digital versatile disc ("DVD") drive, etc. The removable medium 580 is read from and/or written to in a well-known manner. Removable storage medium 580 may be, for example, a floppy disk, magnetic tape, CD, DVD, SD card, etc.

The removable storage medium 580 is a non-transitory computer readable medium having stored thereon computer executable code (i.e., software) and/or data. The computer software or data stored on the removable storage medium 580 is read into the system 550 for execution by the processor 560.

In alternative embodiments, secondary memory 570 may include other similar means for allowing computer programs or other data or instructions to be loaded into the system 550. Such means may include, for example, an external storage medium 595 and an interface 570. Examples of external storage medium 595 may include an external hard disk drive or an external optical drive, or and external magneto-optical drive.

Other examples of secondary memory 570 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage media 580 and communication interface 590, which allow software and data to be transferred from an external medium 595 to the system 550.

System 550 may also include an input/output ("I/O") interface 585. The I/O interface 585 facilitates input from and output to external devices. For example the I/O interface 585 may receive input from a keyboard or mouse and may provide output to a display. The I/O interface 585 is capable of facilitating input from and output to various alternative types of human interface and machine interface devices alike.

System 550 may also include a communication interface 590. The communication interface 590 allows software and data to be transferred between system 550 and external devices (e.g. printers), networks, or information sources. For example, computer software or executable code may be transferred to system 550 from a network server via communication interface 590. Examples of communication interface 590 include a modem, a network interface card ("NIC"), a wireless data card, a communications port, a PCMCIA slot and card, an infrared interface, and an IEEE 1394 fire-wire, just to name a few.

Communication interface 590 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

Software and data transferred via communication interface 590 are generally in the form of electrical communication signals 605. These signals 605 are preferably provided to communication interface 590 via a communication channel 600. In one embodiment, the communication channel 600 may be a wired or wireless network, or any variety of other communication links. Communication channel 600 carries signals 605 and can be implemented using a variety of wired or wireless communication means including wire or cable, fiber optics, conventional phone line, cellular phone link, wireless data communication link, radio frequency ("RF") link, or infrared link, just to name a few.

Computer executable code (i.e., computer programs or software) is stored in the main memory 565 and/or the secondary memory 570. Computer programs can also be received via communication interface 590 and stored in the main memory 565 and/or the secondary memory 570. Such computer programs, when executed, enable the system 550 to perform the various functions of the present invention as previously described.

In this description, the term "computer readable medium" is used to refer to any non-transitory computer readable storage media used to provide computer executable code (e.g., software and computer programs) to the system 550. Examples of these media include main memory 565, secondary memory 570 (including internal memory 575, removable medium 580, and external storage medium 595), and any peripheral device communicatively coupled with communication interface 590 (including a network information server or other network device). These non-transitory computer readable mediums are means for providing executable code, programming instructions, and software to the system 550.

In an embodiment that is implemented using software, the software may be stored on a computer readable medium and loaded into the system 550 by way of removable medium 580, I/O interface 585, or communication interface 590. In such an embodiment, the software is loaded into the system 550 in the form of electrical communication signals 605. The software, when executed by the processor 560, preferably causes the processor 560 to perform the inventive features and functions previously described herein.

The system 550 also includes optional wireless communication components that facilitate wireless communication over a voice and over a data network. The wireless communication components comprise an antenna system 610, a radio system 615 and a baseband system 620. In the system 550, radio frequency ("RF") signals are transmitted and received over the air by the antenna system 610 under the management of the radio system 615.

In one embodiment, the antenna system 610 may comprise one or more antennae and one or more multiplexors (not shown) that perform a switching function to provide the antenna system 610 with transmit and receive signal paths. In the receive path, received RF signals can be coupled from a multiplexor to a low noise amplifier (not shown) that amplifies the received RF signal and sends the amplified signal to the radio system 615.

In alternative embodiments, the radio system 615 may comprise one or more radios that are configured to communicate over various frequencies. In one embodiment, the radio system 615 may combine a demodulator (not shown) and modulator (not shown) in one integrated circuit ("IC"). The demodulator and modulator can also be separate components. In the incoming path, the demodulator strips away the RF carrier signal leaving a baseband receive audio signal, which is sent from the radio system 615 to the baseband system 620.

If the received signal contains audio information, then baseband system 620 decodes the signal and converts it to an analog signal. Then the signal is amplified and sent to a speaker. The baseband system 620 also receives analog audio signals from a microphone. These analog audio signals are converted to digital signals and encoded by the baseband system 620. The baseband system 620 also codes the digital signals for transmission and generates a baseband transmit audio signal that is routed to the modulator portion of the radio system 615. The modulator mixes the baseband transmit audio signal with an RF carrier signal generating an RF transmit signal that is routed to the antenna system and may pass through a power amplifier (not shown). The power amplifier amplifies the RF transmit signal and routes it to the antenna system 610 where the signal is switched to the antenna port for transmission.

The baseband system 620 is also communicatively coupled with the processor 560. The central processing unit 560 has access to data storage areas 565 and 570. The central processing unit 560 is preferably configured to execute instructions (i.e., computer programs or software) that can be stored in the memory 565 or the secondary memory 570. Computer programs can also be received from the baseband processor 610 and stored in the data storage area 565 or in secondary memory 570, or executed upon receipt. Such computer programs, when executed, enable the system 550 to perform the various functions of the present invention as previously described. For example, data storage areas 565 may include various software modules (not shown) that are executable by processor 560.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, and methods described in connection with the embodiments disclosed herein can be implemented or performed with a general purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

What is claimed is:

1. A technical system comprising:
a non-transitory computer readable medium that stores executable programmed server modules;
at least one processor at a server system connected to at least one network, wherein the at least one processor is communicatively coupled with the non-transitory computer readable medium and is configured to execute the programmed server modules, and wherein the programmed server modules are configured to, when executed by the at least one processor at the server system,
receive patient information for a human dementia patient and caregiver information for at least one human caregiver to the dementia patient,
determine patient risk factors for the dementia patient based on the patient information,
determine caregiver risk factors for the at least one caregiver based on the caregiver information, by at least
determining a belief state of the at least one caregiver based on the caregiver information,
determining a willingness of the at least one caregiver to change the belief state based on the caregiver information,
determining one or more competencies of the at least one caregiver based on the caregiver information, and
determining the caregiver risk factors based on the belief state, the willingness to change the belief state, and the one or more competencies of the at least one caregiver,
determine a contribution of the patient risk factors to an acute incident risk, wherein the acute incident risk represents a risk that the dementia patient will experience an acute health incident,
determine a contribution of the caregiver risk factors to the acute incident risk of the dementia patient,
determine a numerical value representing the acute incident risk, based on the determined contributions of the patient risk factors and the caregiver risk factors,
determine a personalized engagement plan for the at least one caregiver to change the belief state of the at least one caregiver, wherein the personalized engagement plan comprises a list of caregiver activities for the at least one caregiver,
deliver the activities to a caregiver device of the at least one caregiver over the at least one network,
identify one or more personalized digital therapies for a patient, based on the patient information, wherein the patient information comprises a current stage of dementia of the dementia patient, and wherein each personalized digital therapy comprises a dose of one or more patient activities for the dementia patient, and
deliver the one or more personalized digital therapies to a patient device of the dementia patient over the at least one network; and
one or more programmed client modules, wherein the programmed client modules are configured to, when executed by at least one processor at the patient device, provide the one or more personalized digital therapies to the dementia patient via the patient device, and, after providing the one or more personalized digital therapies to the dementia patient, take a picture of the dementia patient via the patient device, and send the picture of the dementia patient to the caregiver device.

2. A technical system comprising:
a non-transitory computer readable medium that stores executable programmed server modules;
at least one processor at a server system connected to at least one network, wherein the at least one processor is communicatively coupled with the non-transitory computer readable medium and is configured to execute the programmed server modules, and wherein the programmed server modules are configured to, when executed by the at least one processor at the server system,
receive patient information for a human dementia patient and caregiver information for at least one human caregiver to the dementia patient,
determine patient risk factors for the dementia patient based on the patient information,
determine caregiver risk factors for the at least one caregiver based on the caregiver information, by at least
determining a belief state of the at least one caregiver based on the caregiver information,
determining a willingness of the at least one caregiver to change the belief state based on the caregiver information,
determining one or more competencies of the at least one caregiver based on the caregiver information, and
determining the caregiver risk factors based on the belief state, the willingness to change the belief state, and the one or more competencies of the at least one caregiver,
determine a contribution of the patient risk factors to an acute incident risk, wherein the acute incident risk represents a risk that the dementia patient will experience an acute health incident,
determine a contribution of the caregiver risk factors to the acute incident risk of the dementia patient,
determine a numerical value representing the acute incident risk, based on the determined contributions of the patient risk factors and the caregiver risk factors,
determine a personalized engagement plan for the at least one caregiver to change the belief state of the at least one caregiver, wherein the personalized engagement plan comprises a list of caregiver activities for the at least one caregiver,
deliver the activities to a caregiver device of the at least one caregiver over the at least one network,
identify one or more personalized digital therapies for a patient, based on the patient information, wherein the patient information comprises a current stage of dementia of the dementia patient, and wherein each personalized digital therapy comprises a dose of one or more patient activities for the dementia patient, and
deliver the one or more personalized digital therapies to a patient device of the dementia patient over the at least one network; and
one or more programmed client modules, wherein the programmed client modules are configured to, when executed by at least one processor at the caregiver device, simultaneously display, on a display of the caregiver device, the one or more personalized digital therapies being provided to the dementia patient at the patient device, and
video of the dementia patient while the one or more personalized digital therapies are being provided to the dementia patient at the patient device.

3. The system of claim 2, wherein the programmed server modules further, periodically:
newly determine the at least one caregiver's belief state,
update the caregiver risk factors and the personalized engagement plan, based on the newly determined belief state, and
update the numerical value representing the acute incident risk, based on the updated caregiver risk factors.

4. The system of claim 2, wherein the dose is based on the time of day the one or more personalized digital therapies are administered to the dementia patient.

5. The system of claim 2, wherein the dose is based on a cognitive state of the dementia patient.

6. The system of claim 2, wherein the programmed server modules, when executed by the at least one processor at the server system, routes messages from the caregiver device to a patient device of the dementia patient by, for each message:
receiving the message from the caregiver device over the at least one network;
determining whether or not to filter the message based on the patient information, including a current state of awareness or agitation of the patient; and,
when determining not to filter the message, delivering the message to the patient device over the at least one network.

7. The system of claim 2, wherein the programmed server modules further:
store a library comprising non-personal content for use with a plurality of patients;
store a library comprising personal content of the dementia patient for use with only the dementia patient; and
dynamically combine the non-personal content with the personal content to generate the one or more personalized digital therapies.

8. The system of claim 7, wherein the personal content comprises a photograph of one or more family members of the dementia patient, and wherein the programmed server modules further deliver an indication to the caregiver device to provide more personal content for the dementia patient.

9. The system of claim 2, wherein the programmed client modules further provide a color code on the display to indicate a type of psychosocial therapy represented by a current one of the one or more personalized digital therapies that is being provided to the dementia patient at the patient device.

10. The system of claim 2, wherein the programmed client modules further display a measure of the dementia patient's engagement with the one or more personalized digital therapies being provided to the dementia patient at the patient device, based on an analysis of the dementia patient's eye movements.

11. The system of claim 2, wherein the programmed client modules further display an image of a human brain that highlights regions of the human brain that are synchronously stimulated by a psychosocial therapy represented by a current one of the one or more personalized digital therapies that is being provided to the dementia patient at the patient device.

12. The system of claim 2, wherein the patient risk factors comprise social environment risk.

13. The system of claim 2, wherein the programmed server modules generate a dashboard for display at the caregiver device, wherein the dashboard comprises a first representation of the numerical value, representing the acute incident risk, and a relationship between the numerical value and a peer group value.

14. The system of claim 13, wherein the programmed server modules further:
calculate a numerical caregiver-burden value, representing a burden on the at least one caregiver, based on one or both of the patient information and the caregiver information;
a numerical quality-of-life value, representing a quality of life of the at least one caregiver;
a numerical total-engagement value, representing an engagement level of the at least one caregiver; and
a numerical caregiver-support value, representing a level of support available to the at least one caregiver,
wherein the dashboard further comprises representations of the numerical caregiver-burden value, the numerical quality-of-life value, the numerical total-engagement value, and the numerical caregiver-support value.

15. The system of claim 2, wherein the programmed server modules provide one of education or training to the at least one caregiver via the caregiver device, and wherein the education or training is configured to be personalized to the at least one caregiver based on a specific type of dementia of the dementia patient.

16. The system of claim 15, wherein the education or training is configured to be personalized to the at least one caregiver based on a current belief state of the at least one caregiver.

17. The system of claim 16, wherein the education or training is configured to improve the current belief state of the at least one caregiver.

18. The system of claim 15, wherein the programmed server modules provide education to the at least one caregiver via the caregiver device, and wherein the education is configured to be personalized to the at least one caregiver based on a specific stage of the specific type of dementia of the dementia patient.

19. The system of claim 18, wherein the programmed server modules provide education to the at least one caregiver via the caregiver device, and wherein the education is configured to be personalized to the at least one caregiver based on specific comorbidities of the specific type of dementia of the dementia patient.

20. The system of claim 19, wherein the specific comorbidities correspond to the specific stage of the specific type of dementia of the dementia patient.

21. The system of claim 15, wherein the programmed server modules are configured to pace the providing of one of education or training to the at least one caregiver based on a specific need of the at least one caregiver.

22. The system of claim 15, wherein a content of the education or training comprises a story provided as a video on the caregiver device and is configured to become an experience of the at least one caregiver.

23. The system of claim 2, wherein the programmed server modules are configured to establish a therapy session between the at least one caregiver and a human therapist via the caregiver device.

24. The system of claim 2, wherein the programmed server modules are configured to:
match a plurality of caregivers based on individual caregiver characteristics;

create a caregiver support group comprising matched caregivers; and establish a collaborative communication session between caregivers of the caregiver support group via the respective caregiver device of each caregiver in the caregiver support group.

\* \* \* \* \*

UNITED STATES PATENT AND TRADEMARK OFFICE
CERTIFICATE OF CORRECTION

PATENT NO. : 11,315,694 B2
APPLICATION NO. : 14/557918
DATED : April 26, 2022
INVENTOR(S) : Dirk Soenksen et al.

Page 1 of 1

It is certified that error appears in the above-identified patent and that said Letters Patent is hereby corrected as shown below:

On the Title Page

In Item (60), under "Related U.S. Application Data", in Column 1, Line 2, after "Provisional application No. 61/910,803, filed on Dec. 2, 2013." insert -- provisional application No. 61/989,264 filed on May 6, 2014 and provisional application No. 62/047,557 filed on Sept. 8, 2014 --.

Signed and Sealed this
Eighteenth Day of April, 2023

Katherine Kelly Vidal
*Director of the United States Patent and Trademark Office*